US00PP18092P2

(12) United States Plant Patent
Olesen

(10) Patent No.: US PP18,092 P2
(45) Date of Patent: Sep. 25, 2007

(54) FLORIBUNDA ROSE PLANT NAMED 'POULCAS022'

(50) Latin Name: ***Rosa* hybrid**
Varietal Denomination: Poulcas022

(75) Inventor: Mogens Nyegaard Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 0 days.

(21) Appl. No.: 11/389,463

(22) Filed: Mar. 23, 2006

(51) Int. Cl.
*A01H 5/00* (2006.01)

(52) U.S. Cl. ..... Plt./150
(58) Field of Classification Search ..... Plt./149, Plt./148, 150
See application file for complete search history.

*Primary Examiner*—Kent Bell
*Assistant Examiner*—June Hwu

(57) ABSTRACT

A new garden rose plant of the floribunda class which has abundant, red flowers and attractive foliage. This new and distinct variety has shown to be uniform and stable in the resulting generations from asexual propagation.

1 Drawing Sheet

Botanical designation: *Rosa* hybrid.
Variety denomination: 'Poulcas022'.

SUMMARY OF THE INVENTION

The present invention constitutes a new and distinct variety of garden rose plant which originated from a controlled crossing between the female seed parent, 'Poulskov', U.S. Plant Pat. No. 9,062, and the male pollen parent, an unnamed seedling.

The two parents were crossed during the summer of 1991 and the resulting seeds were planted in a controlled environment in Fredensborg, Denmark. The new variety, named 'Poulcas022', originated as a single seedling from the stated cross.

The new variety may be distinguished from its female seed parent by the following combination of characteristics:

1. Flowers of the seed parent are 60 to 80 mm in diameter. Flowers of 'Poulcas022' are normally 55 mm in diameter.
2. Flowers of the seed parent have a general tonality of Red Group 49D and 56B. Flowers of 'Poulcas022' are Red Group 41C to Red Group 43D.

The new variety may be distinguished from its male pollen parent by the following combination of characteristics:

1. The pollen parent has flowers which are lighter pink than flowers of 'Poulcas022'.
2. The pollen parent has fewer flower petals than those of 'Poulcas022'.

The objective of the hybridization of this rose variety was to create a new and distinct variety for garden use with unique qualities, such as:

1. Uniform and abundant red flowers with long lasting quality;
2. Vigorous, but compact growth when propagated both as a budded rose and on its own roots;
3. Exceptional disease resistance.

This combination of qualities is not present in previously available commercial cultivars of this type, known to the inventor, and distinguish 'Poulcas022' from all other varieties of which we are aware.

As part of the rose development program, Mogens N. Olesen germinated the seeds from the aforementioned hybridization during winter of 1991 and conducted evaluations on the resulting seedlings in a controlled environment in Fredensborg, Denmark. 'Poulcas022' was selected in the spring of 1992 by the inventor as a single plant from the progeny of the aforementioned hybridization.

Asexual reproduction of 'Poulcas022' by traditional budding and rooted cuttings was first done by Mogens N. Olesen in the nursery in Fredensborg, Denmark in July, 1992. This initial and other subsequent asexual propagations conducted in controlled environments have demonstrated that the characteristics of 'Poulcas022' are true to type and are transmitted from one generation to the next.

BRIEF DESCRIPTION OF THE DRAWING

The accompanying color illustration shows as true as is reasonably possible to obtain in color photographs of this type, the typical characteristics of the buds, flowers, leaves, and stems, of 'Poulcas022'. Specifically illustrated in the drawing are.

DETAILED DESCRIPTION OF THE VARIETY

Figures 1A, 1B, 1C, 1D, 1E, 1F, 1G:
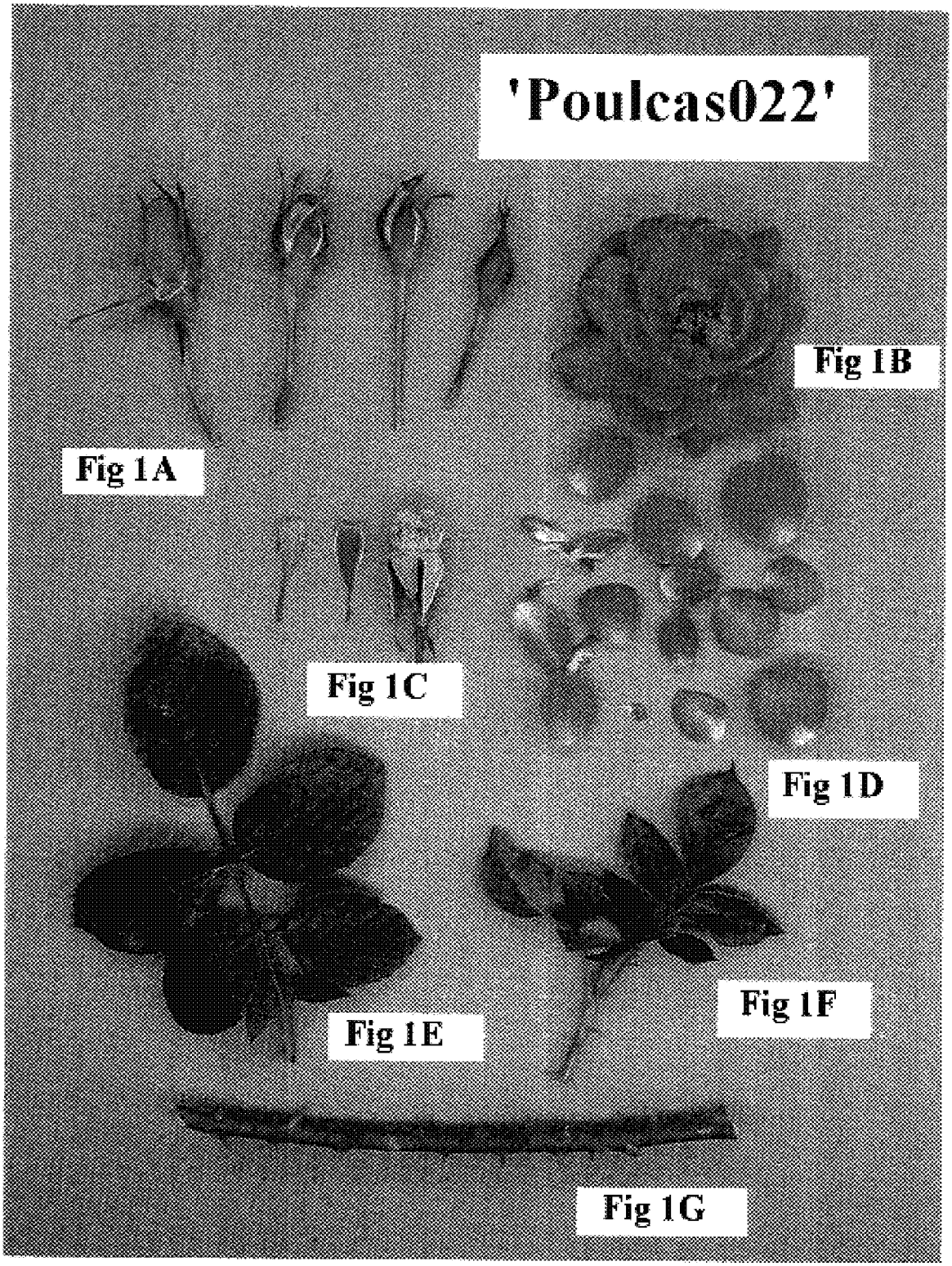
FIG. 1A; Flower buds at various stages of development.
FIG. 1B; Open flower.
FIG. 1C; Sepals and reproductive parts.
FIG. 1D; Flower petals, detached.
FIG. 1E; Mature leaf.
FIG. 1F; Juvenile leaf.
FIG. 1G; Bare stem.

The following is a description of 'Poulcas022', as observed in its growth in in a field nursery in Jackson County, Oreg. Observed plants are 3 years of age, and were grown on *Rosa multiflora* understock. Color references are made using The Royal Horticultural Society (London, England) Colour Chart, 2001, except where common terms of color are used.

For a comparison, several physical characteristics of the rose variety 'Poulriber', U.S. Plant Pat. No. 12,902, are compared to 'Poulcas022' in Chart 1.

CHART 1

| | 'Poulcas022' | 'Poulriber' |
|---|---|---|
| Petal Count | 40 petals total, 10 of which are petaloids | 18 to 22 petals |
| Flower Diameter | 55 mm | 65 to 70 mm |
| General Tonality of Flower Color | Red Group 41C to Red Group 43D | Red Group 40C to Red Group 41B |

FLOWER AND FLOWER BUD

Blooming habit: Continuous.

Flower bud:

*Size.*—Upon opening, 14 mm in length from base of receptacle to end of bud. Bud diameter is 23 mm.

*Bud form.*—Urceolate.

*Bud color.*—As sepals unfold, petals are Red Group 52C with intonations of Yellow-White Group 158B.

*Sepal inner surface.*—Color: Yellow-Green Group 147C. Surface: Medium pubescence observed.

*Sepal outer surface.*—Color: Yellow-Green Group 144A. Texture: Smooth.

*Sepal shape.*—Apex: Cirrhose. Base: Flat at union with receptacle.

*Sepal margin.*—Margins have weak foliaceous appendages on three of the five sepals.

*Sepal size.*—Normally 25 mm long by 7 mm wide.

*Receptacle.*—Texture: Smooth. Shape: Urn-shaped. Size: 10 mm (h)×8 mm (w). Color: Yellow-Green Group 144A. Anthocyanic pigments the color of Greyed-Orange Group 166A observed.

*Pedicel.*—Surface: Smooth. Length: 40 to 45 mm. Diameter: 2 mm. Color: Yellow-Green Group 144A with anthocyanic pigments of Greyed-Orange Group 166A. Strength: Strong.

Flower bud development: Flower buds are borne singularly and in clusters of an average of 7 flower buds per stem.

Flower bloom:

*Fragrance.*—Light floral.

*Duration.*—The blooms have a duration on the plant of approximately 7 to 10 days. Petals fall cleanly away from plant after flowers have fully matured.

*Size.*—Flower diameter is normally 55 mm when open. Flower depth is 25 mm on average.

*Flower shape.*—General shape is an open cup with reproductive flower parts partially exposed. Shape of flower, side view: Upon opening the upper portion is flattened convex. The lower portion is flat. After opening, the upper portion is flattened convex. The lower portion is concave.

*Petalage.*—Under normal conditions, flowers have 40 petals total, 10 of which are petaloids.

*Petal color.*—Upon opening, outer petals Upper surface: Red Group 52C to Red Group 41C. Lower surface: Red-Purple Group 58D to Red Group 52D. Upon opening, inner petals: Upper surface: Red Group 43D to Red Group 41C. Lower surface: Red Group 48D to Red Group 52D. Basal petal spots, upon opening: Upper surface: Yellow-Green Group 150C to Yellow Group 1D. Lower surface: Yellow-Green Group 150C. After opening, outer petals Upper surface: Red Group 52D to Red Group 41D. Lower surface: Red Group 52D. After opening, inner petals: Upper surface: Red Group 52D to Red Group 41D. Lower surface: Red Group 52D. Basal petal spots, after opening: Upper surface: Yellow-Green Group 150C to Yellow Group 1D. Lower surface: Yellow-Green Group 150C.

General tonality: On open flower Red Group 41C to Red Group 43D. No change in the general tonality at the end of the 10th day.

Petals:

*Petal reflex.*—None.

*Margin.*—Entire and uniform.

*Shape.*—Generally narrow elliptical in shape. Apex shape: Orbicular. Base shape: Acute to obtuse.

*Size.*—Upper surface: 33 mm (l)×32 mm (w). Lower surface: 29 mm (l)×20 mm (w).

*Texture.*—Smooth.

*Thickness.*—Average.

*Arrangement.*—Not Formal.

Petaloids:

*Quantity.*—Normally 10.

*Shape.*—Narrow elliptical.

*Color.*—Upper surface: Red Group 43D to 41C. Lower surface: Red Group 48D to Red Group 52C.

*Size.*—On average, 15 mm (l)×10 mm (w).

Reproductive organs:

*Pollen.*—None observed.

*Anthers.*—Size: 2 mm in length. Color: Yellow-Orange Group 17A. Quantity: Normally 180.

*Filaments.*—Color: Yellow Group 5C. Length: 7 mm.

*Pistils.*—Length: 11 mm. Quantity: Normally 80 to 85.

*Stigmas.*—Superior in location relative to the length of the filaments and the height of the anthers. Color: Yellow Group 9D.

*Styles.*—Color: Yellow-Green Group 150D.

*Hips.*—None Observed in the field nursery in Jackson County Oreg.

PLANT

Plant growth: Upright to bushy. When grown as a budded field grown plant on *Rosa multiflora* understock, the average height of the plant is 60 to 100 cm and the average width is 75 cm.

Stems:

*Color.*—: Juvenile growth: Yellow-Green Group 146C. Mature growth: Yellow-Green Group 146A.

*Length.*—On average, canes are 60 cm from the base of the plant to the flowering portion.

*Diameter.*—5 mm.

*Internodes.*—On mature canes, there is an average distance of 22 mm between nodes.

*Surface texture.*—Young wood: Smooth. Older wood: Smooth.

Prickles:

*Incidence.*—17 prickles per 10 cm of stem.

*Size.*—Average length of prickles on mature stems is 13 mm.

*Shape.*—Upper side: Linear. Lower side: Concave.

*Color.*—Juvenile prickles: Yellow-Green Group 145B to 145C. Mature prickles: Greyed-Orange Group 166B to Greyed-Orange Group 177C.

Plant foliage: Normal number of leaflets leaves in middle of the stem: 7 leaflets.

*Compound leaf.*—130 mm (l)×95 (w).

*Quantity.*—3 leaves per 10 cm of stem on average.

*Color of mature foliage.*—Upper side: Yellow-Green Group 147A. Lower side: Yellow-Green Group 147B.

*Color of juvenile foliage.*—Upper side: Yellow-Green Group 146A. Lower side: Yellow-Green Group 146A to 146B.

Plant leaves and leaflets:

*Stipules.*—Size: 20 mm in length. Shape: Linear, slightly broad based with outward extending apecies. Margins: Finely serrated with few stipitate glands. Color: Yellow-Green Group 146B. Anthocyanin: None observed.

*Petiole.*—Length: Normally 20 mm. Diameter: 2 mm on average.

*Upper surface.*—Color: Yellow-Green Group 146B.

*Lower surface.*—Color: Yellow-Green Group 144A. Observations: No stipitate glands and few prickles observed.

*Rachis.*—Length: Normally 55 mm Upper surface: Color: Yellow-Green Group 146B.

*Lower surface.*—Color: Yellow-Green Group 144A. Observations: No stipitate glands and few prickles observed.

*Leaflet.*—Edge: Serrated. Size: Average size of the terminal leaflet on normal leaves is 50 mm in length by 40 mm wide. Shape: Generally orbicular. Base: Rounded. Apex: Cuspidate. Texture: Smooth. Thickness: Average. Arrangement: Odd pinnate. Venation: Reticulate. Glossiness: Moderate finish.

Disease resistance: Above average resistance to powdery and downy mildew, rust, black spot, and *Botrytis* under normal growing conditions in Jackson County, Oreg.

Cold hardiness: The variety is tolerant to USDA Cold Hardiness Zone 6.

Heat tolerance: The variety has been found to be suitable for climate conditions found in the American Horticulture Society heat zone 7.

It is claimed:

1. A new and distinct variety of rose plant of the floribunda rose class named 'Poulcas022', substantially as illustrated and described herein, due to its abundant red flowers, disease resistance, and extended period of bloom.

* * * * *

'Poulcas022'